US011602540B2

(12) United States Patent
Morganstern et al.

(10) Patent No.: US 11,602,540 B2
(45) Date of Patent: *Mar. 14, 2023

(54) METHOD FOR STIMULATING BLOOD FLOW IN A PENILE REGION OF A PATIENT

(71) Applicant: BMR MEDICAL LLC, Marietta, GA (US)

(72) Inventors: Steven Morganstern, Sandy Springs, GA (US); Carlos Becerra, Atlanta, GA (US)

(73) Assignee: BMR Medical LLC, Marietta, GA (US)

( * ) Notice: Subject to any disclaimer, the term of this patent is extended or adjusted under 35 U.S.C. 154(b) by 627 days.

This patent is subject to a terminal disclaimer.

(21) Appl. No.: 16/587,975

(22) Filed: Sep. 30, 2019

(65) Prior Publication Data
US 2020/0093857 A1 Mar. 26, 2020

Related U.S. Application Data

(63) Continuation-in-part of application No. 15/132,418, filed on Apr. 19, 2016, now Pat. No. 10,426,835.

(51) Int. Cl.
A61K 33/00 (2006.01)
A61K 31/275 (2006.01)
A61K 31/522 (2006.01)
A61K 31/198 (2006.01)
A61B 5/00 (2006.01)
A61H 1/02 (2006.01)
A61K 9/00 (2006.01)
A61K 31/12 (2006.01)

(52) U.S. Cl.
CPC ............ *A61K 33/00* (2013.01); *A61B 5/0037* (2013.01); *A61H 1/0218* (2013.01); *A61K 9/0019* (2013.01); *A61K 31/12* (2013.01); *A61K 31/198* (2013.01); *A61K 31/275* (2013.01); *A61K 31/522* (2013.01); *A61H 2205/087* (2013.01)

(58) Field of Classification Search
CPC ............ A61P 15/00; A61P 15/10; A61P 15/12
See application file for complete search history.

(56) References Cited

U.S. PATENT DOCUMENTS

| 5,554,103 | A | ‡ | 9/1996 | Zheng | A61B 5/0535 601/15 |
| 5,997,540 | A | ‡ | 12/1999 | Zheng | A61B 5/0535 606/64 |
| 6,251,076 | B1 | ‡ | 6/2001 | Hovland | A61B 5/4393 600/45 |
| 6,572,621 | B1 | ‡ | 6/2003 | Zheng | A61B 5/0535 606/64 |
| 6,589,267 | B1 | ‡ | 7/2003 | Hui | A61G 7/05776 601/15 |
| 6,620,116 | B2 | ‡ | 9/2003 | Lewis | A61H 9/0078 601/15 |
| 6,858,012 | B2 | ‡ | 2/2005 | Burns | A61B 5/0205 600/48 |
| 6,863,670 | B2 | ‡ | 3/2005 | Zheng | A61B 5/0535 601/15 |
| 6,962,599 | B2 | ‡ | 11/2005 | Hui | A61G 7/05776 606/20 |
| 7,048,702 | B2 | ‡ | 5/2006 | Hui | A61H 9/0078 601/15 |
| 7,314,478 | B2 | ‡ | 1/2008 | Hui | A61G 7/05776 606/20 |
| 7,517,312 | B2 | ‡ | 4/2009 | Loeb | A61H 99/00 600/16 |
| 7,713,211 | B2 | ‡ | 5/2010 | Anderson | A61B 5/02007 600/48 |
| 7,981,066 | B2 | ‡ | 7/2011 | Lewis | A61H 9/0078 601/14 |
| 9,132,245 | B2 | ‡ | 9/2015 | Mantell | A61M 13/003 |
| 10,426,835 | B2 | * | 10/2019 | Morganstern | A61K 47/02 |
| 10,987,273 | B2 | * | 4/2021 | Morganstern | A61F 5/41 |
| 2006/0216338 | A1 | ‡ | 9/2006 | Easterling | A61K 9/0014 424/449 |
| 2012/0215142 | A1 | ‡ | 8/2012 | Spector | A61B 17/2251 601/46 |
| 2013/0245541 | A1 | ‡ | 9/2013 | Mantell | A61M 13/003 604/26 |

(Continued)

FOREIGN PATENT DOCUMENTS

RU 2 256 405 ‡ 7/2005

OTHER PUBLICATIONS

Abern (Journal of Sexual Medicine vol. 9 pp. 288-295 published 2012) . (Year: 2012).*
Gelbard (Journal of Urology vol. 187 pp. 2268-2274 published 2012) (Year: 2012).*
Fabrizio et al.: "Experience of Carboxytherapy in Conservative Treatment of Peyronie's disease"; XXI Congresso Nazionale Roma, Associazione Urologi Italiani; 2012.‡
Hind et al.: "Initial results of treatment with Linear Shockwave Therapy (LSWT) by Renova in patients with Erectile Dysfunction"; believed to have been published Aug. 30, 2013.‡
Stein: "Endothelial Dysfunction, Erectile Dysfunction, and Coronary Heart Disease: The Pathophysiologic and Clinical Linkage"; Reviews in Urology; 2003.‡

(Continued)

*Primary Examiner* — Theodore R. Howell
*Assistant Examiner* — George W Kosturko
(74) *Attorney, Agent, or Firm* — Barnes & Thornburg LLP; Jeffrey R. Stone

(57) ABSTRACT

In a method of treating a patient having low blood flow that may be caused by diffused plaque and/or a plaque mass associated with Peyronie's disease in a penile region, a predetermined amount of carbon dioxide is injected into affected corpus cavernosum at a location that is adjacent to, but spaced away from the plaque mass. In addition, either before and/or after the injection of the carbon dioxide, a decalcifying agent(s) may be injected directly into the plaque mass.

20 Claims, 17 Drawing Sheets

(56) References Cited

U.S. PATENT DOCUMENTS

| | | | | |
|---|---|---|---|---|
| 2015/0073312 | A1‡ | 3/2015 | Ein-Gal | A61N 7/00 601/4 |
| 2017/0258674 | A1‡ | 9/2017 | Morganstern | A61H 9/0092 |

OTHER PUBLICATIONS

Notification of related application: U.S. Appl. No. 15/064,162, filed by Morganstern et al., filed Mar. 8, 2016 is commonly owned with the present application and may contain related subject matter.‡

Reisman et al: "Initial experience with linear focused shockwave treatment for erectile dysfunction: a 6-month follow-up pilot study"; International Journal of Impotence Research (2014), 1-5; Oct. 18, 2014.‡

Froschemaier et al.: "Enhanced External Counterpulsation as a New Treatment Modality for Patients with Erectile Dysfunction"; Urologia Internationals; Jul. 20, 1998.‡

Gruenwald et al.: "Shockwave treatment of erectile dysfunction"; https://beta.openaire.eu/search/publication?articleId=od; 2013.‡ www.bodyrenewal.co.za: "Barboxytherapy for Sexual Rejuvenation / Erectile Dysfunction"; Sep. 9, 2015.‡

Anti-Aging Medical Systems: "Carboxy Pen"; believed to have published on Apr. 24, 2013.‡ www.bodyrenewal.co.za: "Carboxytherapy for Sexual Rejuvenation / Erectile Dysfunction", Sep. 9, 2015.

Gruenwald et al.: "Shockwave treatment of erectile dysfunction", https://beta.openaire.eu/search/publication?article=od; 2013.

Hind et al.: "Initial results of treatment with Linear Shockwave Therapy (LZSWZT) by Renova in patients with Erectile Dysfunction", believed to have been published Aug. 30, 2013.

\* cited by examiner
‡ imported from a related application

METHOD FOR STIMULATING BLOOD FLOW IN A PENILE REGION OF A PATIENT

CROSS-REFERENCE TO RELATED APPLICATIONS

This application is a continuation-in-part of U.S. patent application Ser. No. 15/132,418, filed Apr. 19, 2016 and entitled METHOD FOR TREATING PEYRONIE'S DISEASE, the entirety of which of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to treatment methods and, more specifically, to a method of treating Peyronie's disease.

2. Description of the Related Art

Peyronie's disease (also known as induratio penis plastic) is an acquired inflammatory condition of the penis associated with penile curvature. It is a connective tissue disorder involving the growth of fibrous plaques in the soft tissue of the penis. Scar tissue forms in the tunica albuginea, the thick sheath of tissue surrounding the corpora cavernosa causing pain, abnormal curvature, erectile dysfunction, indentation, loss of girth and shortening. The penile curvature of Peyronie's disease is caused by an inelastic scar, or plaque (which may include calcification), that shortens the involved aspect of the tunica albuginea of the corpora cavernosa during erection.

If left untreated, Peyronie's disease may cause fibrotic, nonexpansile thickening of relatively discrete areas of the corpora tunica, typically resulting in focal bend, pain or other functional or structural abnormalities of the erect penis. Surgery is one method of treating Peyronie's disease. Surgery has the disadvantage of being expensive and occasionally resulting in unwanted complications. Several medical treatments have been applied, but results so far have been limited. Surgical treatments have also been used to treat Peyronie's disease. Collagenase Clostridium histolyticum (marketed as Xiaflex), an injectable drug, is the most common medical treatment of Peyronie's disease. It is believed that this works by breaking down the excess collagen in the penis that causes Peyronie's disease. This drug has limited success and it can be quite expensive.

Therefore, there is a need for a reliable and inexpensive non-surgical treatment for Peyronie's disease.

SUMMARY OF THE INVENTION

The disadvantages of the prior art are overcome by the present invention which, in one aspect, is a method of treating a patient having diffused plaque and a plaque mass associated with Peyronie's disease in a penile region, in which a battery of tests is performed to quantify an initial state of parameters associated with Peyronie's disease in the patient. Low intensity shock wave therapy is applied to the plaque mass in the penile region, thereby softening the plaque mass and disrupting any calcification in the plaque mass. Carbon dioxide is injected into the plaque mass. The battery of tests is repeated to quantify a current state of parameters associated with Peyronie's disease in the patient and the current state is compared to the initial state. The aforementioned treatment steps are repeated until the current state differs from the initial state by at least a predetermined amount.

In another aspect, the invention is a treatment method for a patient having a plaque mass associated with Peyronie's disease in a penile region, in which a battery of tests is performed to quantify an initial state of parameters associated with Peyronie's disease in the patient. Low intensity shock wave therapy is applied to a plaque mass in the penile region for about thirteen treatments over a period of seven to eight weeks including a two week break period of no low intensity shock wave treatment, thereby softening the plaque and disrupting calcification in the plaque mass. A plurality of doses of about 160 cc of carbon dioxide per dose is injected into the plaque mass for a total of 960 cc. A counter pulsation treatment is applied every five days during a period of seven weeks to the patient concurrently with the step of applying low intensity shock wave therapy to further disrupt calcification in the plaque mass. A therapeutically effective dose of Verapamil is injected into a dorsal area of the penile area after the step of applying low intensity shock wave therapy to the plaque mass. The battery of tests is repeated to quantify a current state of parameters associated with Peyronie's disease in the patient and comparing the current state to the initial state. The aforementioned steps are repeated until the current state differs from the initial state by at least a predetermined amount.

Alternatively, Peyronie's disease may be treated by administering by injection one or more therapeutic amounts of carbon dioxide into the corpus cavernosum of a patient, adjacent to but spaced away from the plaque deposit. Decalcifying agent(s) may be injected into the plaque deposit before and/or after the carbon dioxide injections.

These and other aspects of the invention will become apparent from the following description of the preferred embodiments taken in conjunction with the following drawings.

As would be obvious to one skilled in the art, many variations and modifications of the invention may be effected without departing from the spirit and scope of the novel concepts of the disclosure.

DETAILED DESCRIPTION OF THE INVENTION

Figure 1:
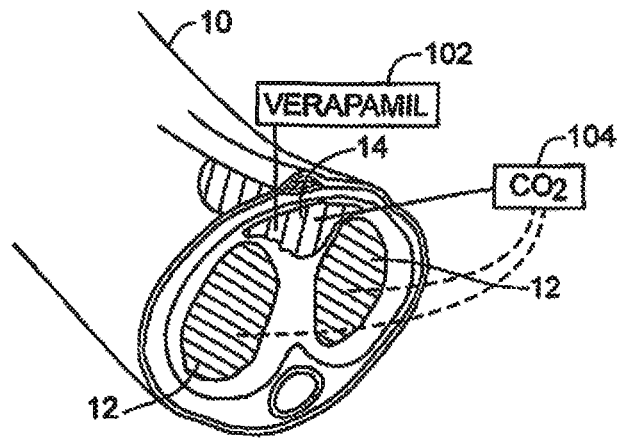
FIG. 1 is a schematic diagram showing treatment of a dorsal plaque.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

As shown in FIG. 1, Peyronie's disease causes curvature of the penis 10 as the result of a plaque mass 14 forming in the dorsal tunica of the penis 10. It can also result from calcification of the corpus cavernosa 12 in the penis 10. As will be shown below, the present treatment protocol includes several steps for improving blood flow through the affected area, along with injecting a therapeutically effective dose of an L-type phenylalkylamine class calcium channel blocker (such as Verapamil) 102 into the plaque mass 14 and also injecting carbon dioxide 104 into the plaque mass 14.

Figure 2:
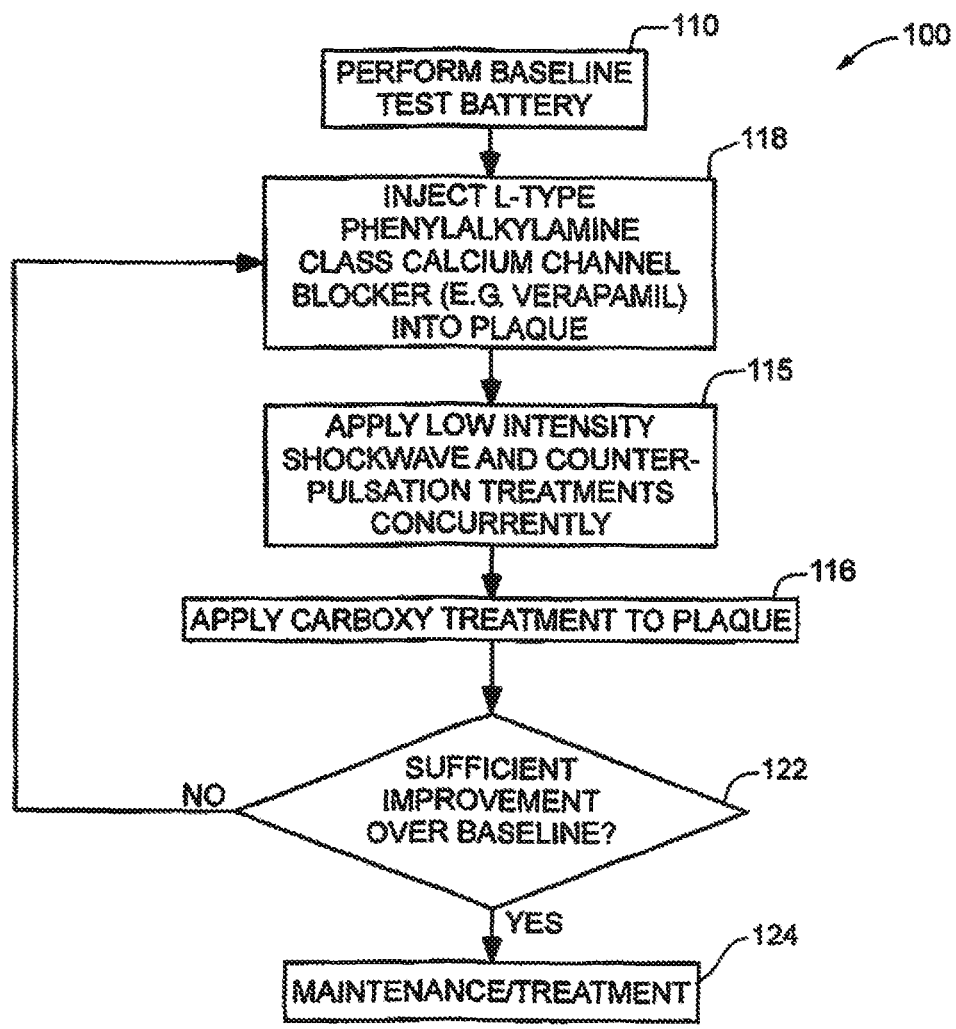
FIG. 2 is a flow chart showing a treatment protocol according to one embodiment of the present invention.

In one embodiment of a treatment protocol 100 for Peyronie's disease, as shown in FIG. 2, comprising performing a baseline test battery 110, injecting an L-type phenylalkylamine class calcium channel blocker, e.g., Verapamil, into the plaque 118, applying low intensity shockwave treatment concurrently with external counter-pulsation treatment, applying carboxy treatment to the plaque 116, then determining if the results of the treatment protocol is sufficient 122 or if the treatment steps beginning with injecting an L-type phenylalkylamine class calcium channel blocker, e.g., Verapamil, into the plaque 118 need to be repeated. If the results are sufficient, then maintenance treatment protocols 124 are followed. Thus, initial test battery is performed on the patient 110 in order to establish a baseline. This test battery typically includes imaging the plaque with an ultrasound imaging device, measuring blood flow in penile blood vessels of the patient with a duplex Doppler ultrasonography blood flow device and measuring pulse wave velocity in a brachial artery and an ankle artery of the patient. Circulatory blood flow velocity in the patient is tested typically with a duplex Doppler. U.S. Pat. No. 6,251,076, issued to Hovland et al., discloses one method of determining blood flow velocity in a penile artery and is incorporated herein by reference for the purpose of disclosing methods of determining blood flow velocity.

Low intensity shock wave therapy is applied to the plaque mass in the penile region 112. This softens the plaque mass and disrupts calcification in the plaque mass. In doing so, low intensity shockwave (LISW) therapy is applied to the plaque mass for about thirteen treatments over a period of seven to eight weeks, including a two week break period off no low intensity shock wave treatment. In the low intensity shockwave treatment (LISW), shock waves having a maximum energy of 0.09 mJmm2 are applied with a local applicator to the penile area once per day for two or three days per week over a course of five weeks. U.S. Publication No. US-2015/0073312-A1, filed by Ein-Gal, discloses one method of low intensity shockwave treatment and is incorporated herein by reference for the purpose of disclosing low intensity shockwave treatment. In a typical treatment, about 300 pulses are applied per minute over the course of between 10 minutes and 20 minutes. The LISW treatment stimulates neovascularization and improves penile blood flow and endothelial function when applied to the corpora cavernosa.

Counter pulsation treatment is applied twice per week during a period of at least ten weeks 114, which can be done concurrently with the low intensity shock wave therapy. This further disrupts calcification in the plaque mass and improves blood flow. The course of external counter-pulsation treatment includes applying external counter-pulsation treatments to the patient for a predetermined number of days per week for a predetermined number of weeks. In applying the course of external counter-pulsation treatments an electrocardiogram (ECG) sensing device is applied to the patient and the ECG is sensed. U.S. Pat. Nos. 7,314,478 and 7,314,478, both issued to Hui, disclose a counter-pulsation apparatus and method for controlling the apparatus and is incorporated herein by reference for the purpose of disclosing counter-pulsation methods. An inflatable cuff is applied to at least one of the patient's calf, lower thigh, upper thigh or buttocks. Typically, cuffs are applied to both of the lower thighs and to both of the upper thighs. Counter pulsations are applied to the cuffs by inflating the cuffs to a pressure of about 300 mm Hg during a diastole sensed by the ECG. Pressure is then rapidly released from the cuffs during onset of the systole, as sensed by the ECG. Counter-pulsations are performed repeatedly during a treatment sessions that last about one hour, which are performed twice per week over a course of ten weeks. (It should be noted that the term "ECP" is sometimes confused with "EECP," which is a registered a trademark for a brand of ECP. However, the EECP brand can be employed as the type of ECP used.

Carbon dioxide is then injected into the plaque mass 116, which is referred to as "carboxy therapy." In this step, about 960 cc of carbon dioxide is injected into one or both of the corpus cavernosum, the dorsal tunica of the patient or other area of plaque mass (typically in injections of about 160 cc each in several different locations). This is typically performed twice per week, but 48 hours apart, for twelve consecutive weeks. Typically, the carboxy therapy is performed after the low intensity shockwave treatment and the counter pulsation treatment steps to reduce the dispersal of the carbon dioxide in the injected tissues. U.S. Pat. No. 9,132,245, issued to Mantell, discloses a carboxy therapy application and is incorporated here by reference to disclose one device and method for administering carboxy therapy. The carboxy therapy infuses carbon dioxide into the tissues, causing the body to interpret the presence of the carbon dioxide as an oxygen deficiency, which results in the production of vascular endothelial growth factors in the tissues.

This encourages vascular growth and local reduction in fat tissue, which results in increased blood flow to the corpora cavernosa.

An L-type phenylalkylamine class calcium channel blocker, of the type known generically as "Verapamil," is injected into a calcified plaque area of the penile area 118.

Typically, in this step 0.625 mg to 2.5 mg of Verapamil is injected into a dorsal tunica of the patient. About 12 Verapamil treatments are administered at a frequency of one every 14 days.

The test battery is repeated 120 to quantify patient treatment progress. If there has not been sufficient improvement over the baseline test, then the treatment steps are repeated 122. Indicia of sufficient improvement include the observance of no plaque in the ultrasound imaging and the observance of a doubling in blood flow in the affected area. Once the desired result is achieved, the patient can return periodically for examination and maintenance treatments 124 if such treatments are indicated.

Alternate embodiments discussed supra for a treatment protocol for Peyronie's disease are illustrated in FIGS. 3-7.

Figure 3:
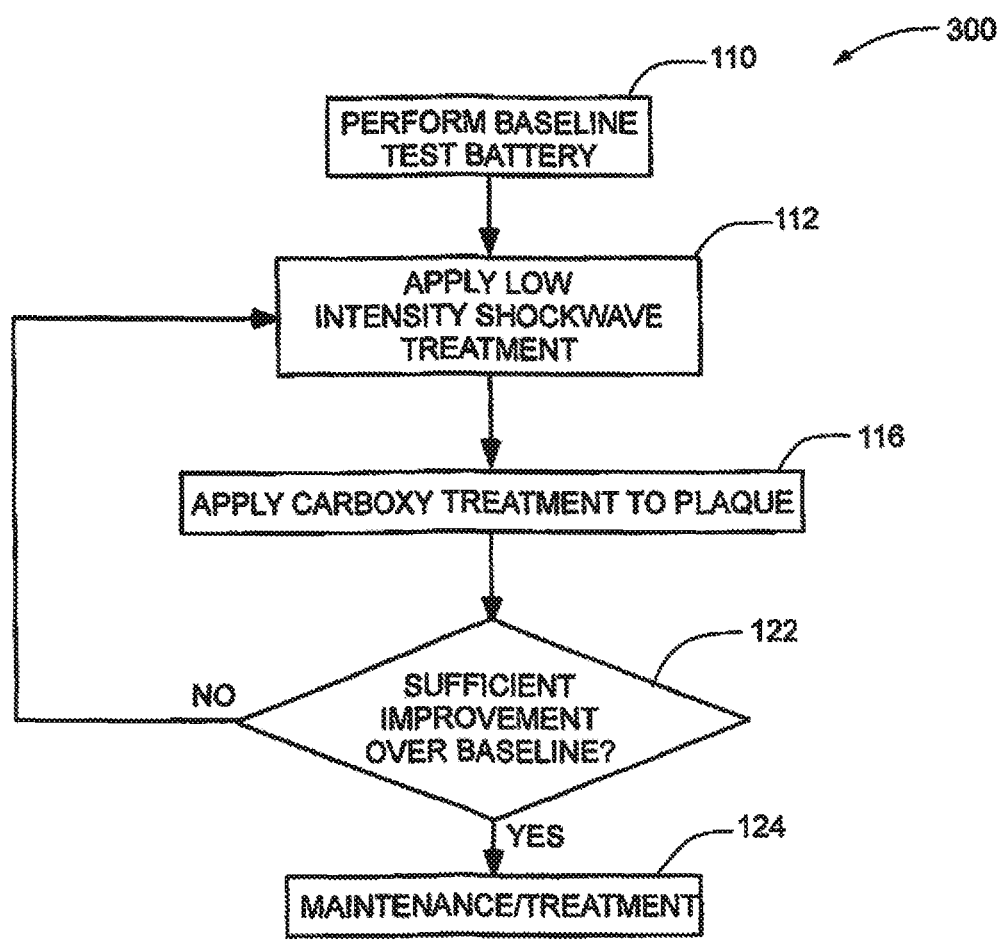
FIG. 3 is a flow chart showing a treatment protocol according to one embodiment of the present invention.

The treatment protocol 300 of FIG. 3 begins with the baseline test battery 110, followed by LISW treatment 112 which is followed by applying the carboxy treatment to the plaque 116, with checking additional test results at 122 to see if results are sufficient. If not, the treatment steps are repeated, beginning with LISW treatment 112 until the test results are sufficiently improved over baseline and maintenance treatments are provided to the patient 124.

Figure 4:
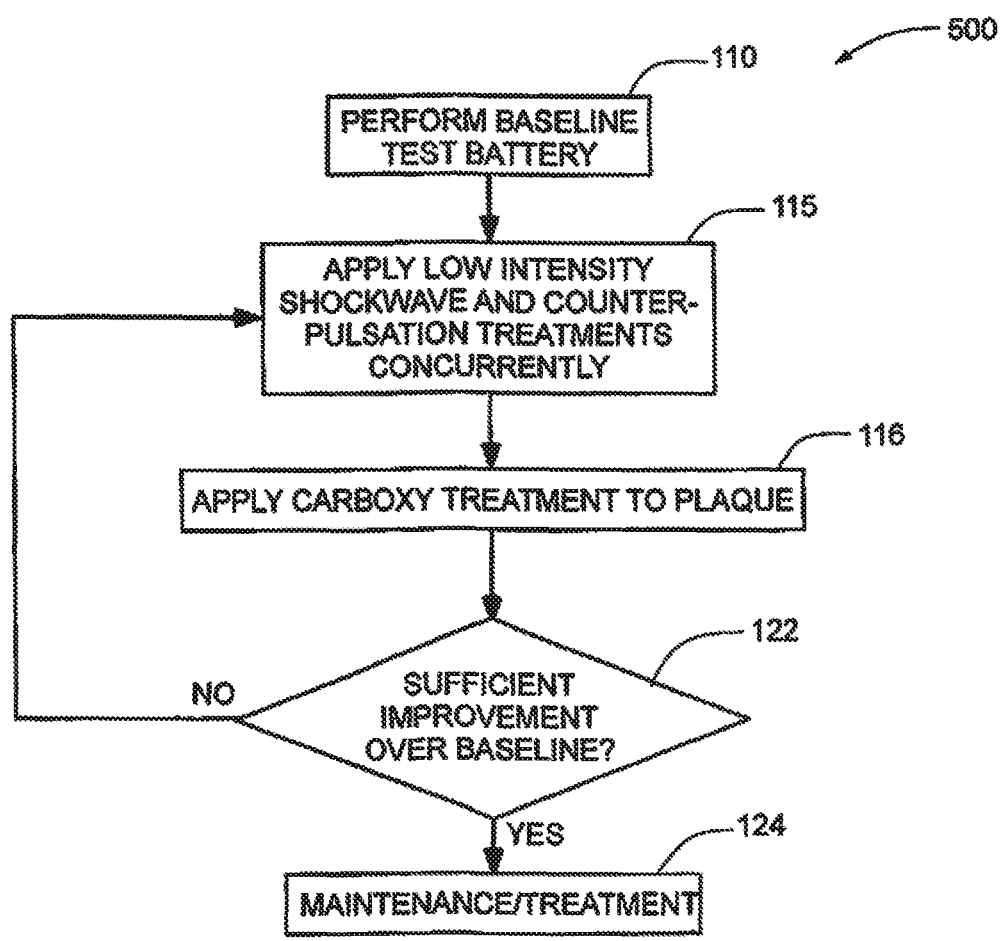
FIG. 4 is a flow chart showing a treatment protocol according to one embodiment of the present invention.

Alternative treatment protocol 500 in FIG. 4 also begins with baseline test battery 100, followed by concurrent treatments of LISW and external counter-pulsation treatments 115. These are followed by applying carboxy treatment 116, with subsequent evaluation of results 122. If insufficient compared with baseline, the steps are repeated beginning with concurrent LISW and counter-pulsation treatments 115 until sufficient test result improvement over baseline is achieved and maintenance treatment protocols are executed 124.

Figure 5:
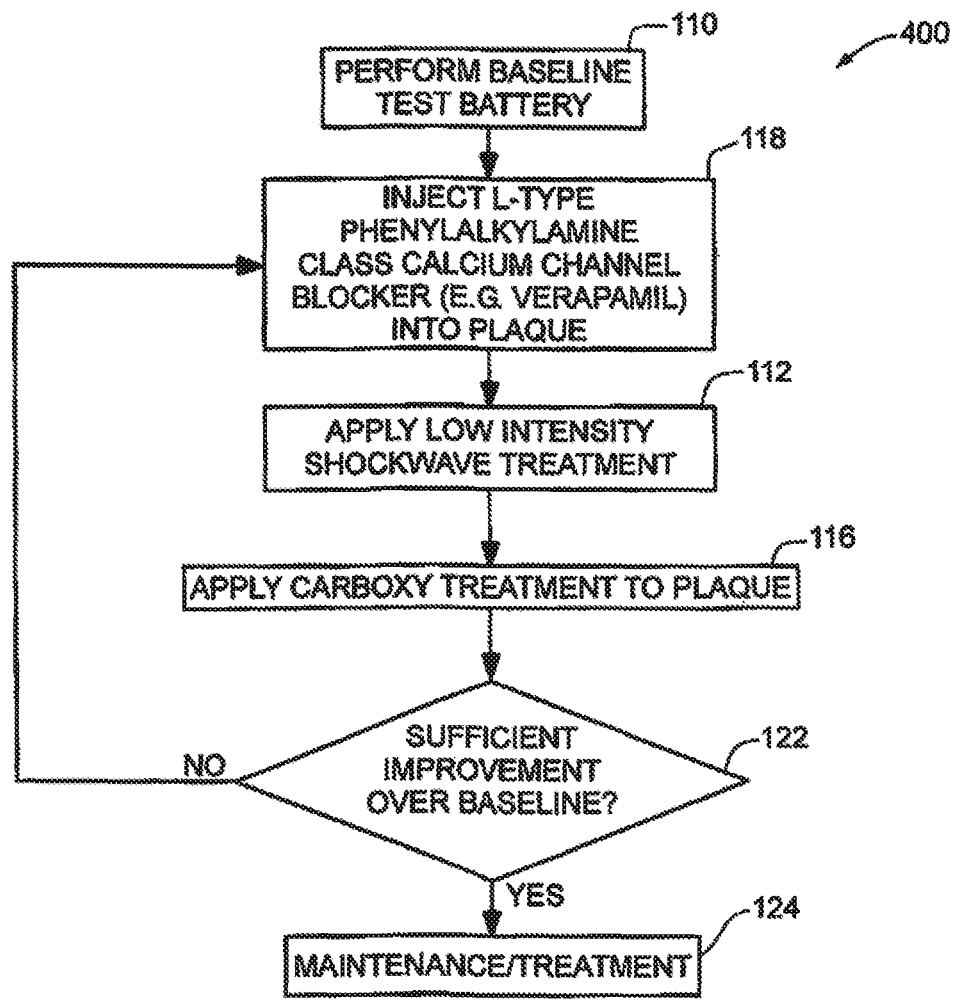
FIG. 5 is a flow chart showing a treatment protocol according to one embodiment of the present invention.

Treatment protocol embodiment 400 of FIG. 5 begins with the baseline test battery 100, followed by injection of the exemplary Verapamil into the plaque 118. This injection is followed by application of LISW treatment 112 which is then followed by application of carboxy treatment to the plaque 116, with subsequent evaluation of results 122. If insufficient compared with baseline, the steps are repeated beginning with injection of the exemplary Verapamil 118 until sufficient test result improvement over baseline is achieved and maintenance treatments 124 are provided to the patient.

Figure 6:
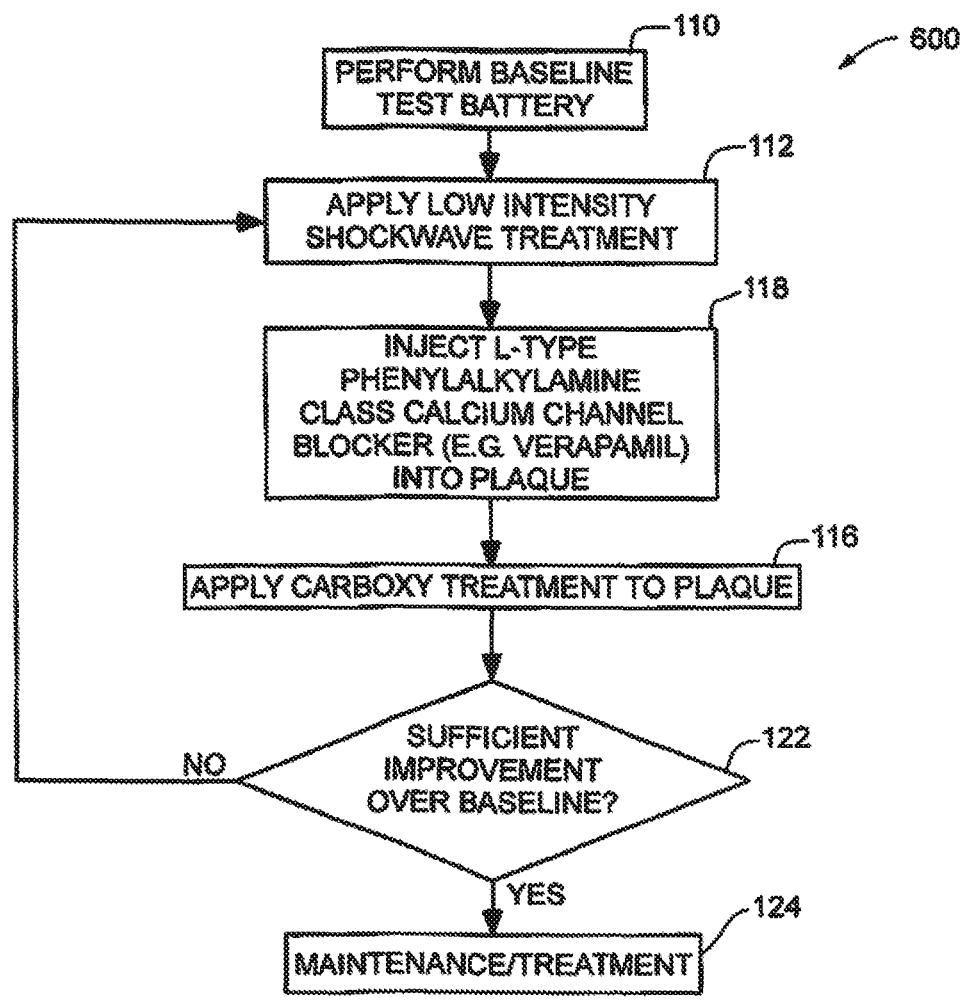
FIG. 6 is a flow chart showing a treatment protocol according to one embodiment of the present invention.

Alternative treatment protocol embodiment 600 of FIG. 6 differs from treatment protocol 400 of FIG. 5 by adding injection of the exemplary Verapamil into the plaque 118 after applying the LISW treatment 112. Next, application of carboxy treatment to the plaque 116 occurs and a decision of insufficient improvement over baseline is made at 122. The repeated steps begin with LISW application at 112 until sufficient improvement over test baseline results are achieved 122 and maintenance treatments 124 are provided to the patient."

The methods of the present invention could also be useful in treating calcification in an individual's hand, or other extremity.

In addition to the above treatment method embodiments for Peyronie's disease, the inventors have learned that, surprisingly, carbon dioxide injections, each injection comprising a therapeutically effective dose, alone can dramatically impact disease progression, softening the plaque to a point where subsequently administered colleganase-based injections can achieve far more significant effectiveness and may dissolve the plaque completely. These carbon dioxide injections preferably administered by one or more direct injections of carbon dioxide into the corpus cavernosum near, but not into, the plaque and may comprise an "over and under" injection of the carbon dioxide at therapeutically effective locations or points proximate or near the plaque within the corpus cavernosum. Here, proximate and/or near the plaque will be well understood by the skilled artisan to be within a therapeutically effective distance of the plaque. However, no matter the approach or access technique, the injection(s) of carbon dioxide into the corpus cavernosum at a point that is near the plaque will also be effective, albeit perhaps less effective than the optimal over and under injection approach or access. Alternatively, one or more of the injection(s) of carbon dioxide may be delivered directly into the plaque within the corpus cavernosum. In some cases, injections of carbon dioxide may be delivered directly into the plaque while others may be delivered into the corpus cavernosum near the plaque, e.g., using an over and under access technique.

Figure 7:
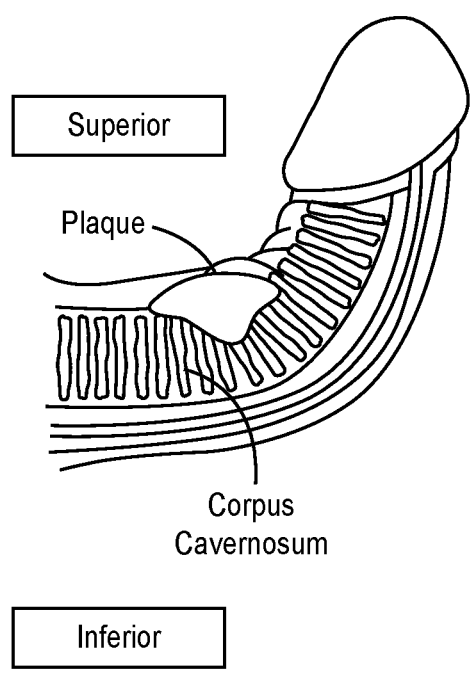
FIG. 7 is a cross-sectional cutaway view of a plaque deposit within one corpus cavernosum.

FIG. 7 illustrates a cross-sectional view of a penis affected by Peyronie's disease and comprising a plaque deposit P residing at least in part within at least one of the corpus cavernosa. The carbon dioxide injection(s) discussed in relation to FIG. 8A et seq., are most optimally made by delivering the dose of carbon dioxide "over" the upper portion of the plaque deposition to a location within the corpus cavernosum that may be over or superior to, the plaque deposit P. Alternatively, the delivery location may be offset to one side of the plaque deposit P.

A second injection of carbon dioxide may be delivered and under, or inferior to, the plaque deposit P, wherein the dose of carbon dioxide is delivered in each case into the corpus cavernosum. The second injection location may be spaced apart from the first injection location and, preferably, on opposing sides of the plaque deposit P, wherein the first and second injection locations are also spaced from the plaque deposit itself, but within a therapeutically effective distance of the plaque deposit P. More than one, i.e., two or more, injections of carbon dioxide may be delivered as above.

As noted, in alternative cases, one or more injections of carbon dioxide dose(s) may be delivered directly into the plaque, either alone or in combination with one or more injections or doses as above that are spaced therapeutically from the plaque P and, therefore also spaced from the dose(s) injected directly into the plaque P.

In all cases the "dose" for each carbon dioxide injection(s) are considered to be "therapeutically effective" which is defined as described above in conjunction with "carboxy therapy".

Figure 8A:
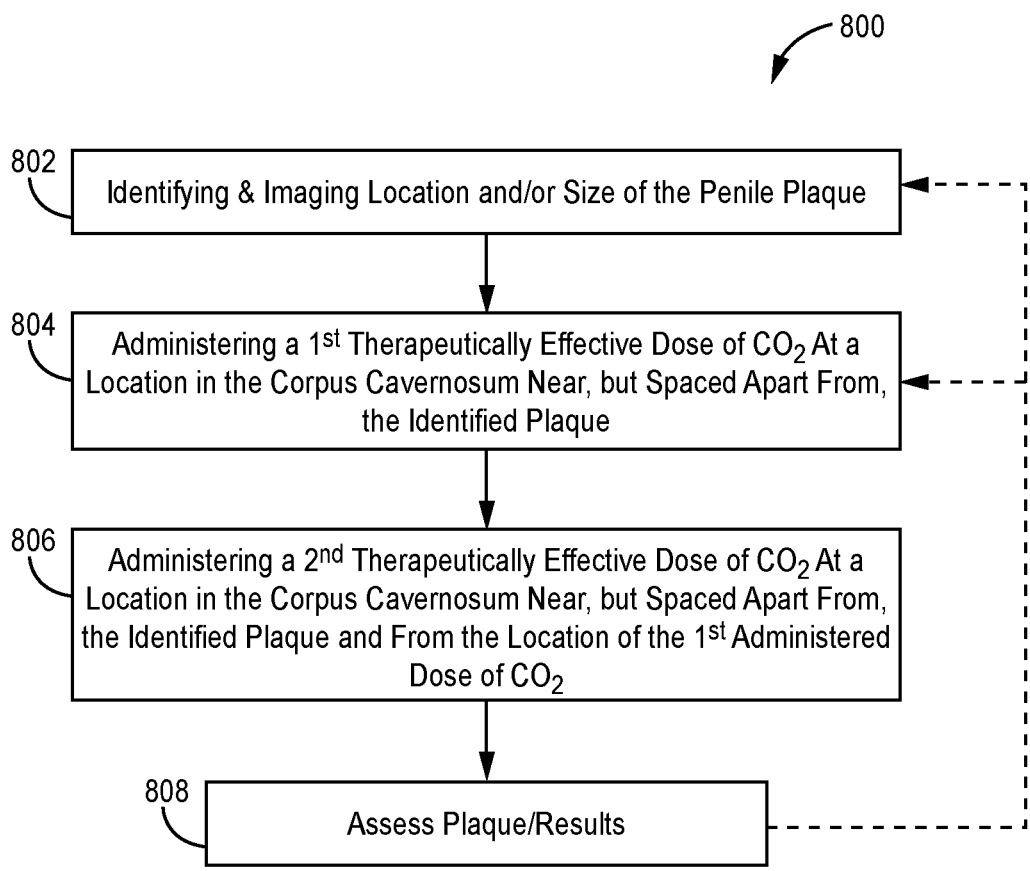
FIG. 8A is one embodiment of a treatment method for Peyronie's disease.

Turning now to FIG. 8A, one embodiment for treating Peyronie's disease is provided. Method 800 may begin at 802 with identifying the location and/or size of the exemplary penile plaque P as in FIG. 7. Next at 804, a first therapeutically effective dose of $CO_2$ may be administered at a location within the affected corpus cavernosum that is close enough to the plaque that at least part of the administered dose will diffuse to the plaque, but that is also spaced apart from the edges of the plaque. Subsequently, at 806, a second therapeutically effective dose of $CO_2$ may be administered within the affected corpus cavernosum at a location that is (1) close enough to the plaque that at least part of the administered dose will diffuse to the plaque, but is also spaced away or apart from the plaque's edges; and (2) spaced apart from the first administered $CO_2$ dose location. At this point, the effects of the treatment may be assessed at 808 and, if necessary or indicated, the process may be repeated, beginning either with step 804 or 802. Note that step 808 may comprise the methodology of step 802 in some embodiments. As in all illustrated embodiments, dashed lines indicate optional method steps.

For all non-direct plaque injections of carbon dioxide, the injection(s) may be administered to a location that is adjacent to but spaced apart or away from the plaque deposit.

Figure 9A:
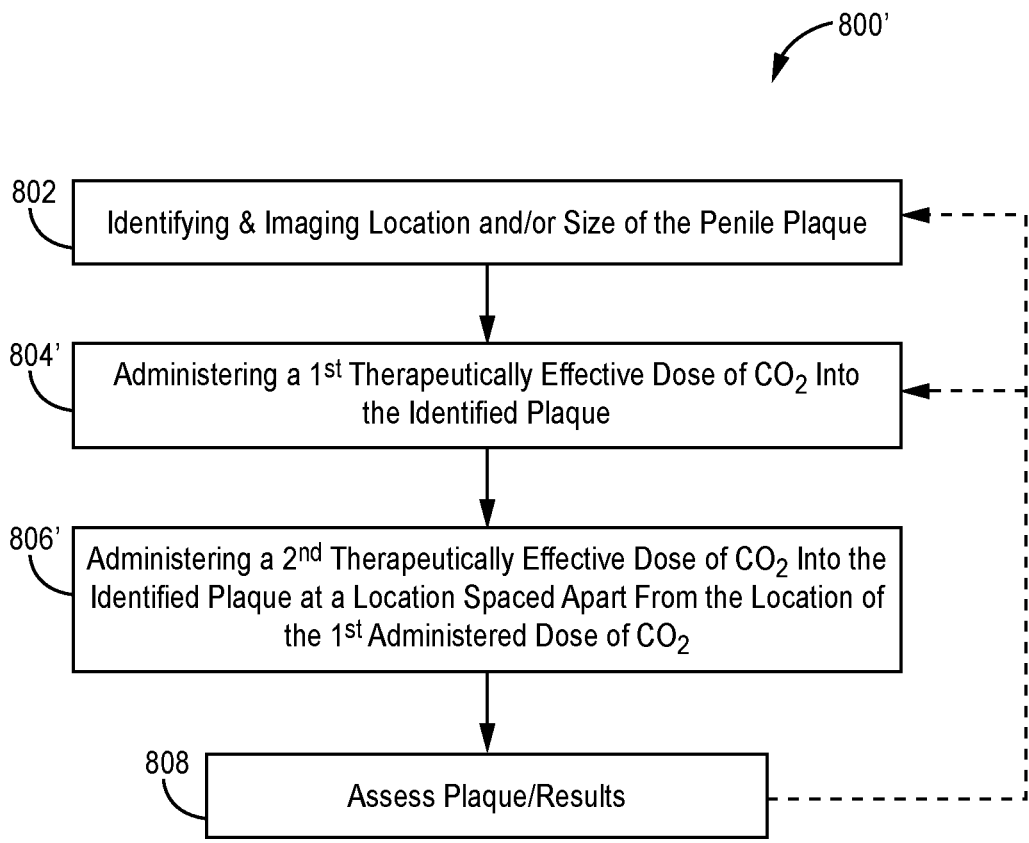
FIG. 9A is one embodiment of a treatment method for Peyronie's disease.

FIG. 9A is a very similar Peyronie's disease treatment method 800' to method 800 of FIG. 8A, except for that, in FIG. 9A, the therapeutically effective doses of $CO_2$ are administered directly into the plaque at 804' and 806'.

Figure 8B:
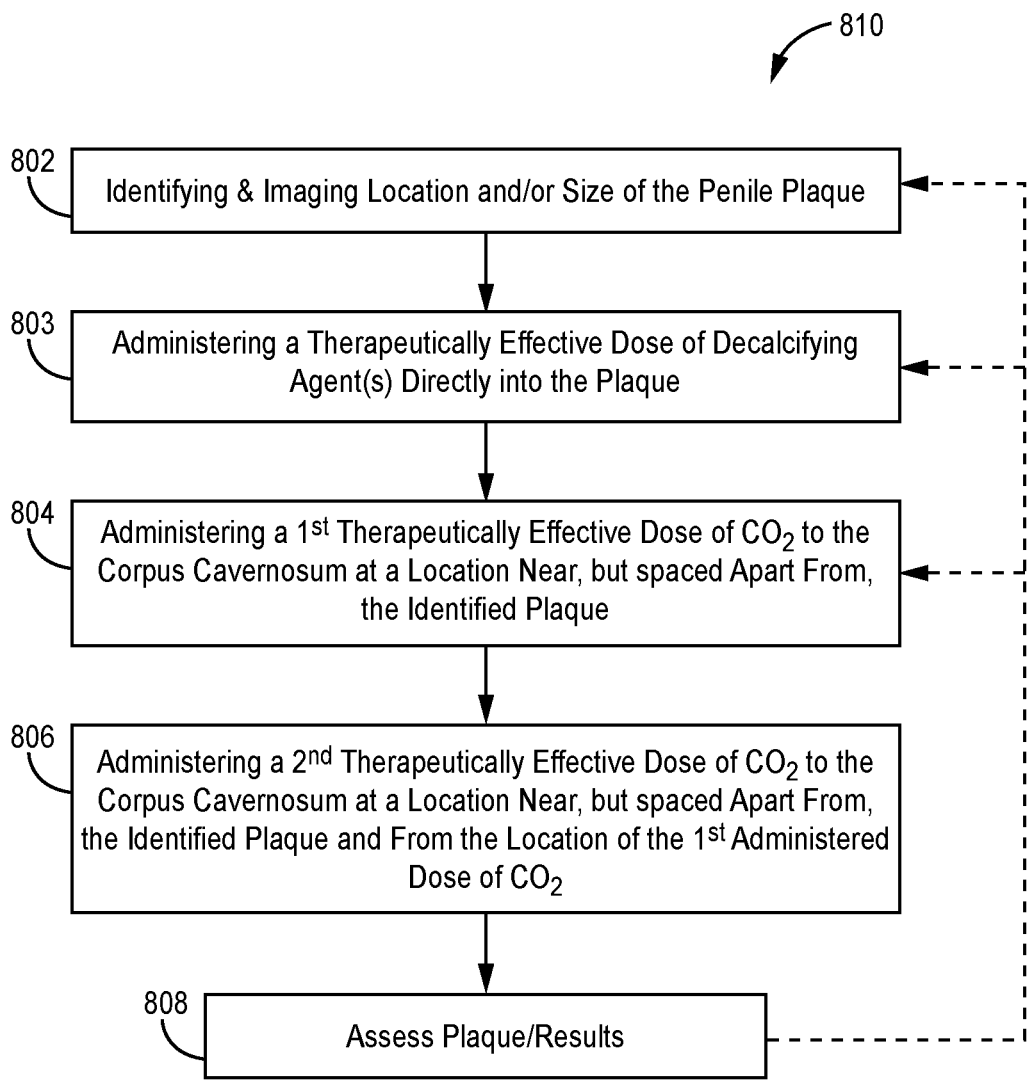
FIG. 8B is one embodiment of a treatment method for Peyronie's disease.

Turning now to FIG. 8B, an alternative method 810 for treating Peyronie's disease is illustrated. Method 810 is identical to method 800 of FIG. 8A, except that step 803 is interposed between steps 802 and 804. Thus, a therapeutically effective dose of a decalcifying agent as described herein is administered by direct injection into the plaque.

Figure 9B:
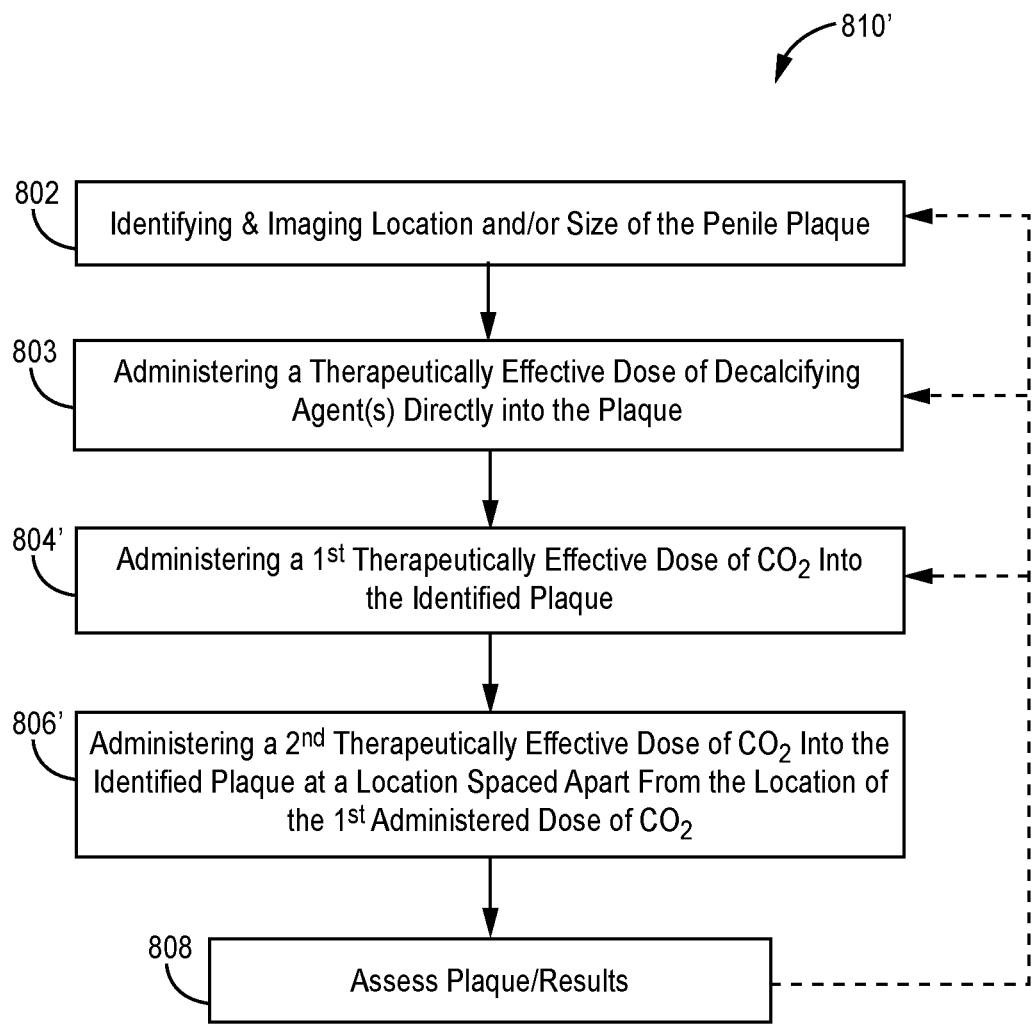
FIG. 9B is one embodiment of a treatment method for Peyronie's disease.

Method 810' of FIG. 9B is, in turn, identical to method 810 FIG. 8B, except that steps 804' and 806' require administration of the $1^{st}$ and $2^{nd}$ therapeutically effective doses of $CO_2$ directly into the identified plaque and further require that the $2^{nd}$ such injection be spaced at a location apart from the location of the $1^{st}$ such injection.

Figure 8C:
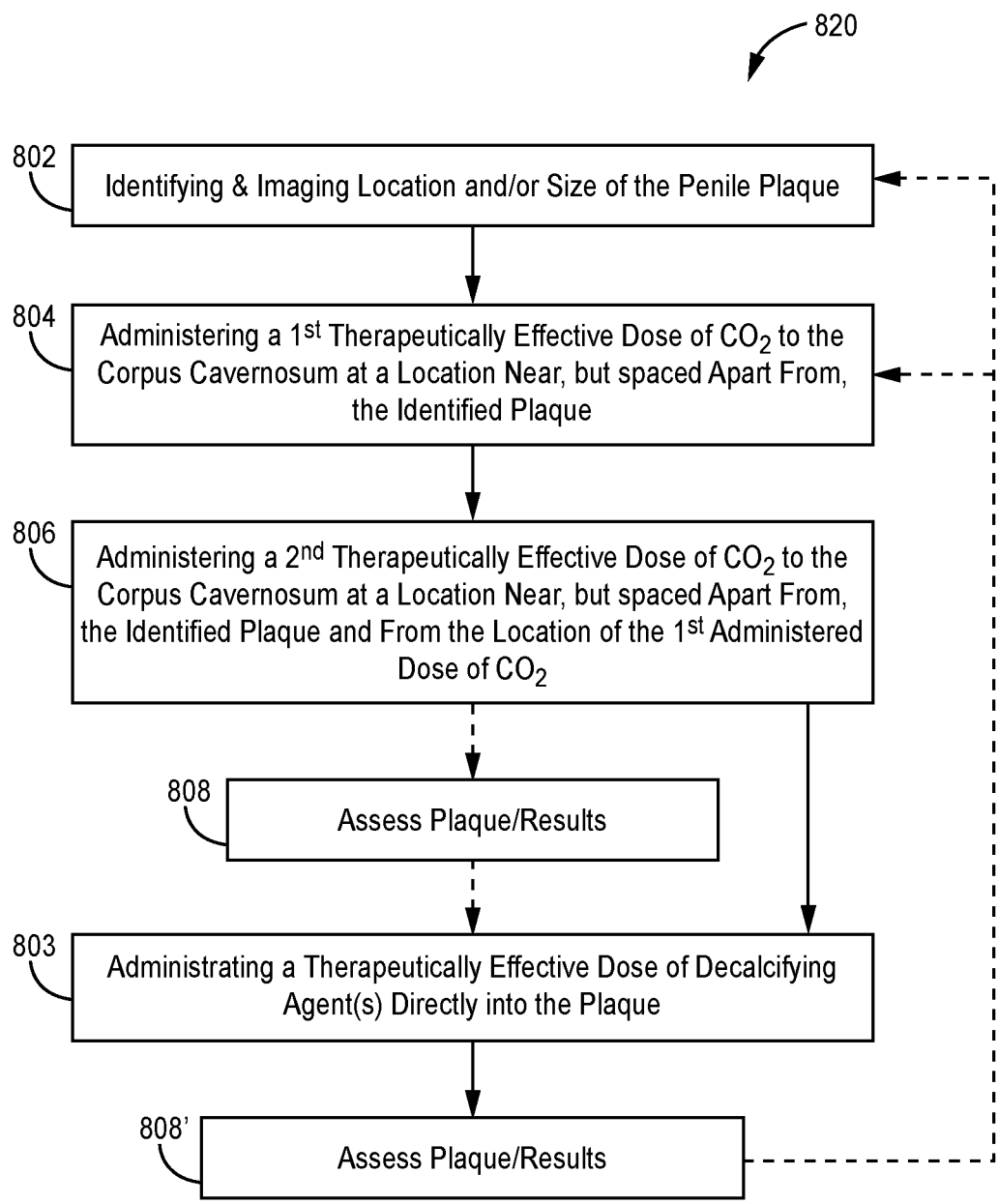
FIG. 8C is one embodiment of a treatment method for Peyronie's disease.

In turn, method 820 of FIG. 8C is identical to method 810 of FIG. 8B, except that step 803 is reordered to occur after execution of the second injection of $CO_2$ at 806 and with the possible interim plaque assessment therebetween at optional step 808. The method 820 concludes with step 808' which may, or may not, be the first plaque assessment step.

Figure 9C:
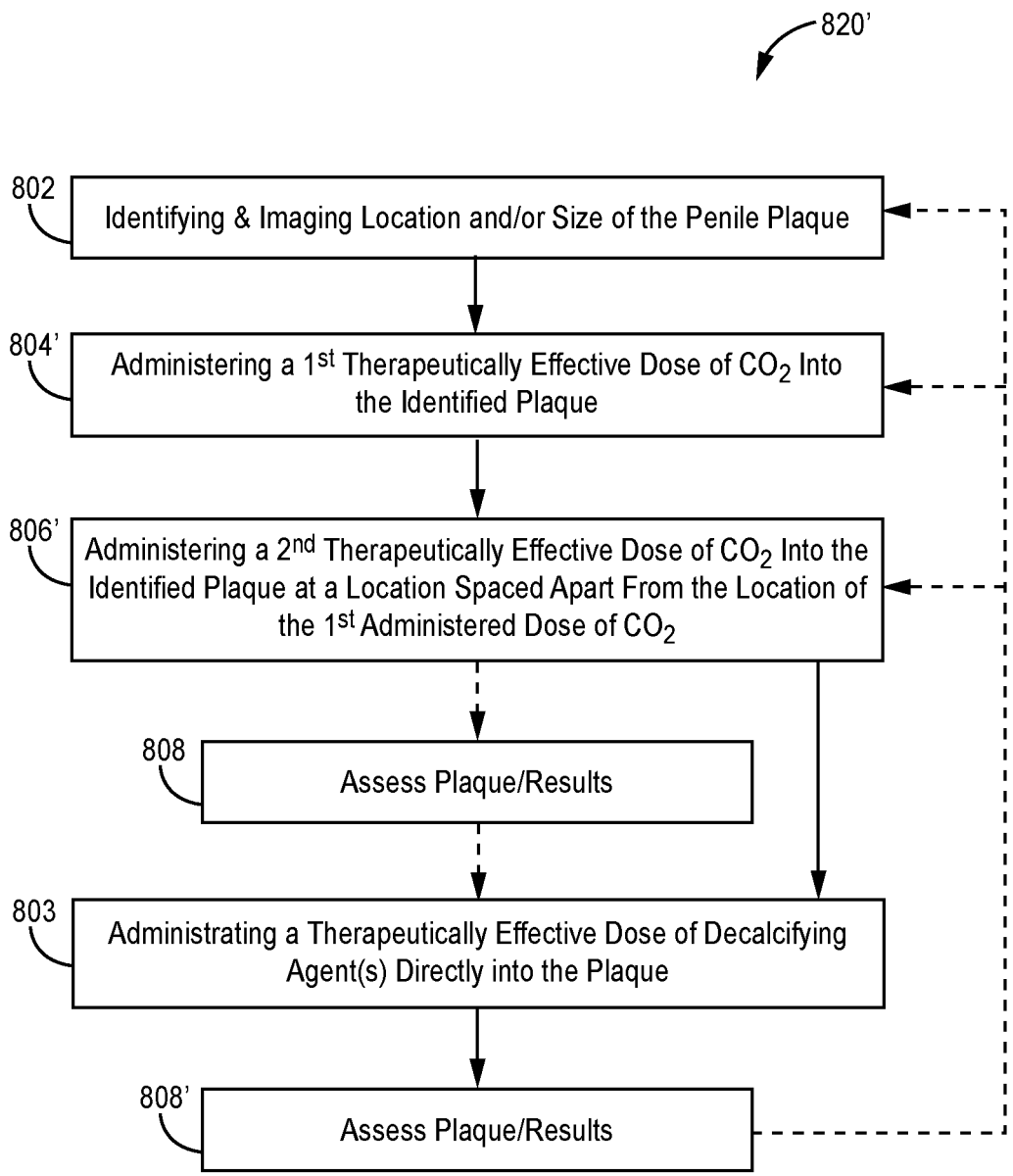
FIG. 9C is one embodiment of a treatment method for Peyronie's disease.

Method 820' of FIG. 9C is, in turn, identical to method 820 of FIG. 8C, with the difference being that the $1^{st}$ and $2^{nd}$ doses of $CO_2$ are injected directly into the plaque deposit and at spaced apart locations from each other within the plaque deposit at steps 804' and 806'.

Figure 8D:
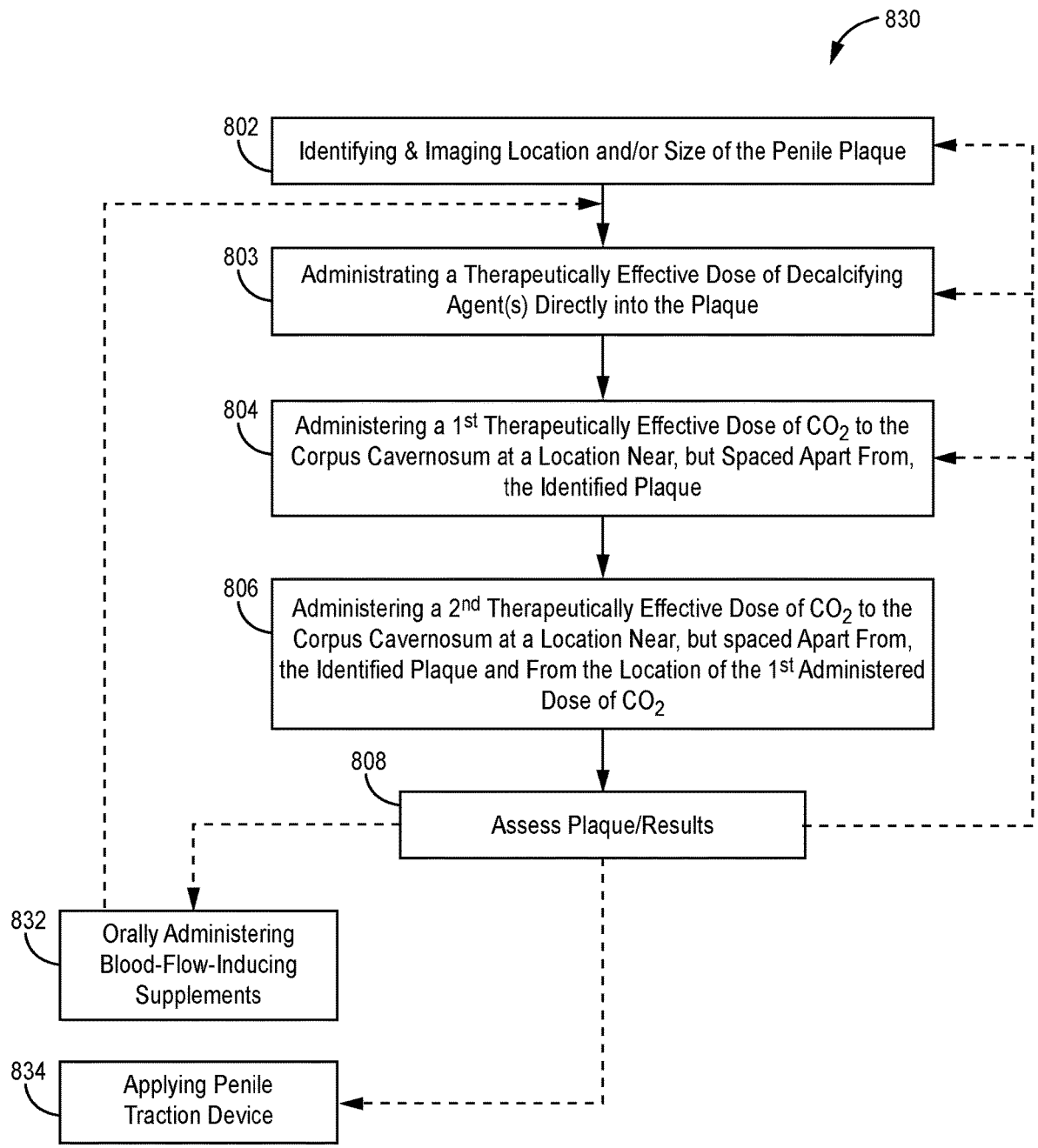
FIG. 8D is one embodiment of a treatment method for Peyronie's disease.

Method 830 of FIG. 8D is identical to method 810 of FIG. 8B, except that two optional steps are included: the oral administration of blood-flow-inducing supplements at 832 and as discussed herein, and applying a penile traction device at 834 as also discussed herein. The dashed lines indicate the optionality of these two method steps 832, 834 and provide possible insertion points into method 830. It will be understood that steps 832 and/or 834 may be effectively inserted at any point in method 830.

Figure 9D:
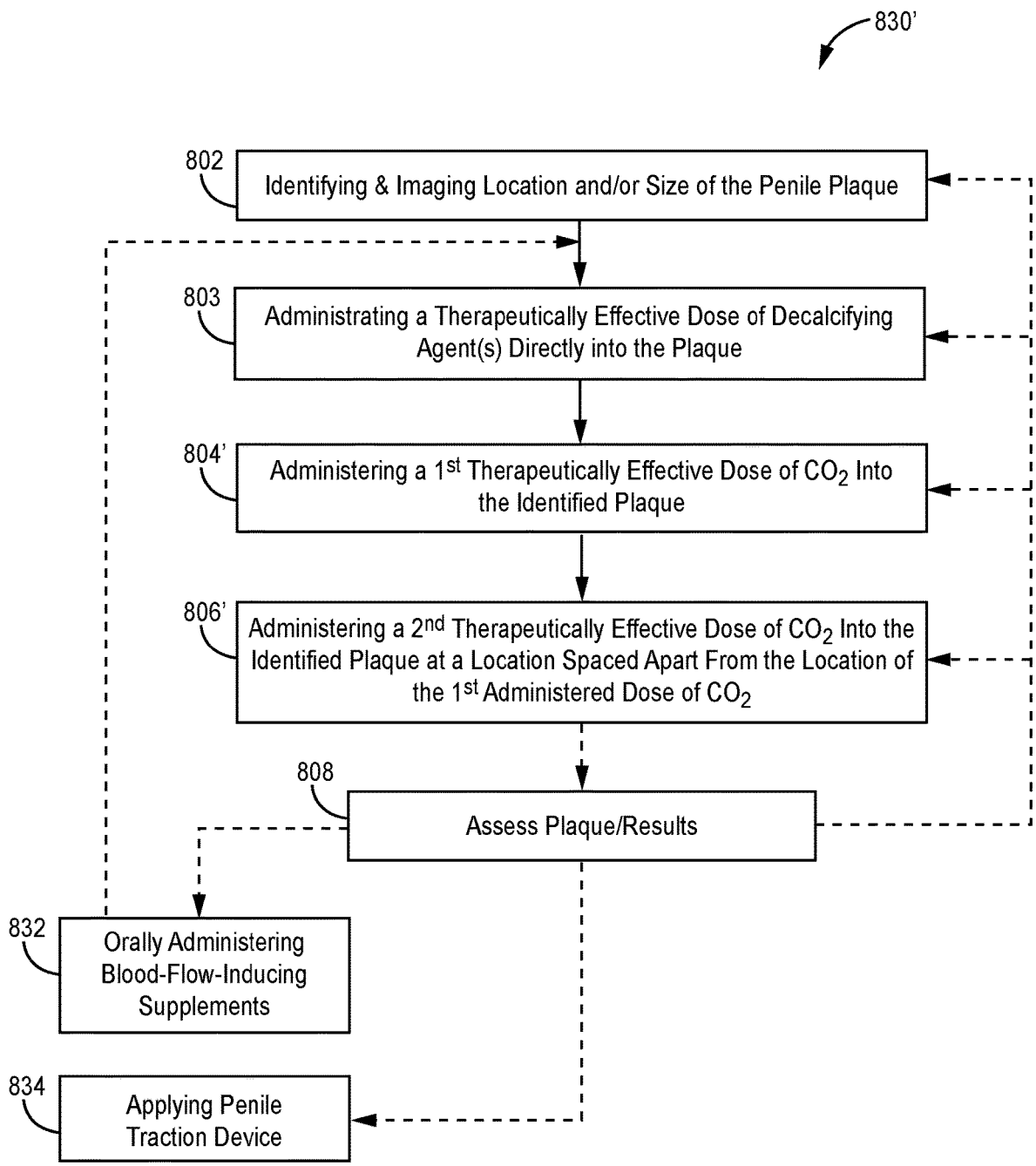
FIG. 9D is one embodiment of a treatment method for Peyronie's disease.

Method 830' of FIG. 9D is identical to method 830 of FIG. 8D except that steps 804' and 806' require the $1^{st}$ and $2^{nd}$ carbon dioxide injections to be delivered into the identified plaque, with the second injection 806' administered at a location within the plaque that is spaced apart from the location of the first injection 804'.

Figure 8E:
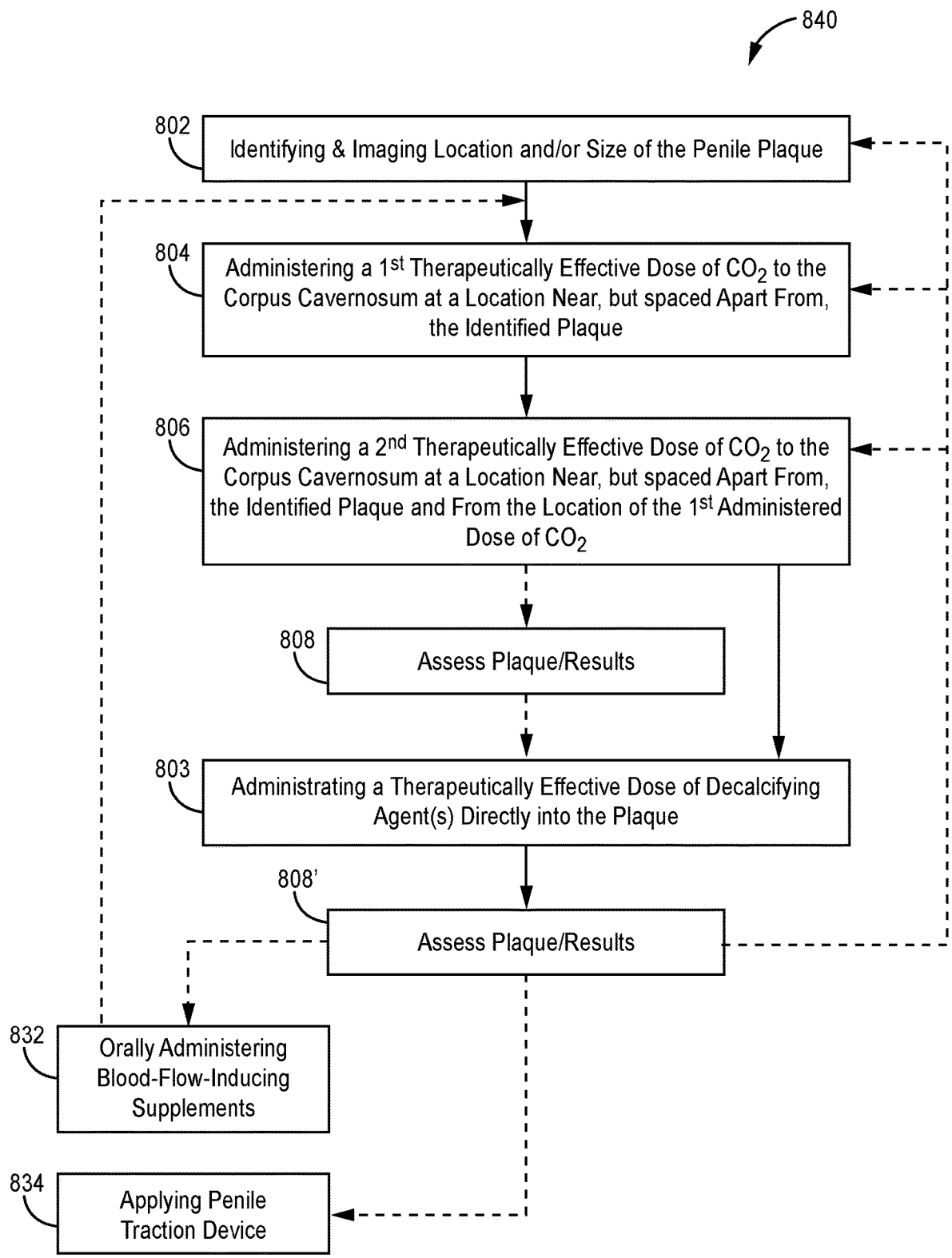
FIG. 8E is one embodiment of a treatment method for Peyronie's disease.

Method 840 of FIG. 8E is identical to method 820 of FIG. 8C, except that two optional steps are included: the oral administration of blood-flow-inducing supplements at 832 and as discussed herein, and applying a penile traction device at 834 as also discussed herein. The dashed lines indicate the optionality of these two method steps 832, 834 and provide possible insertion points into method 840. It will be understood that steps 832 and/or 834 may be effectively inserted at any point in method 840.

Figure 9E:
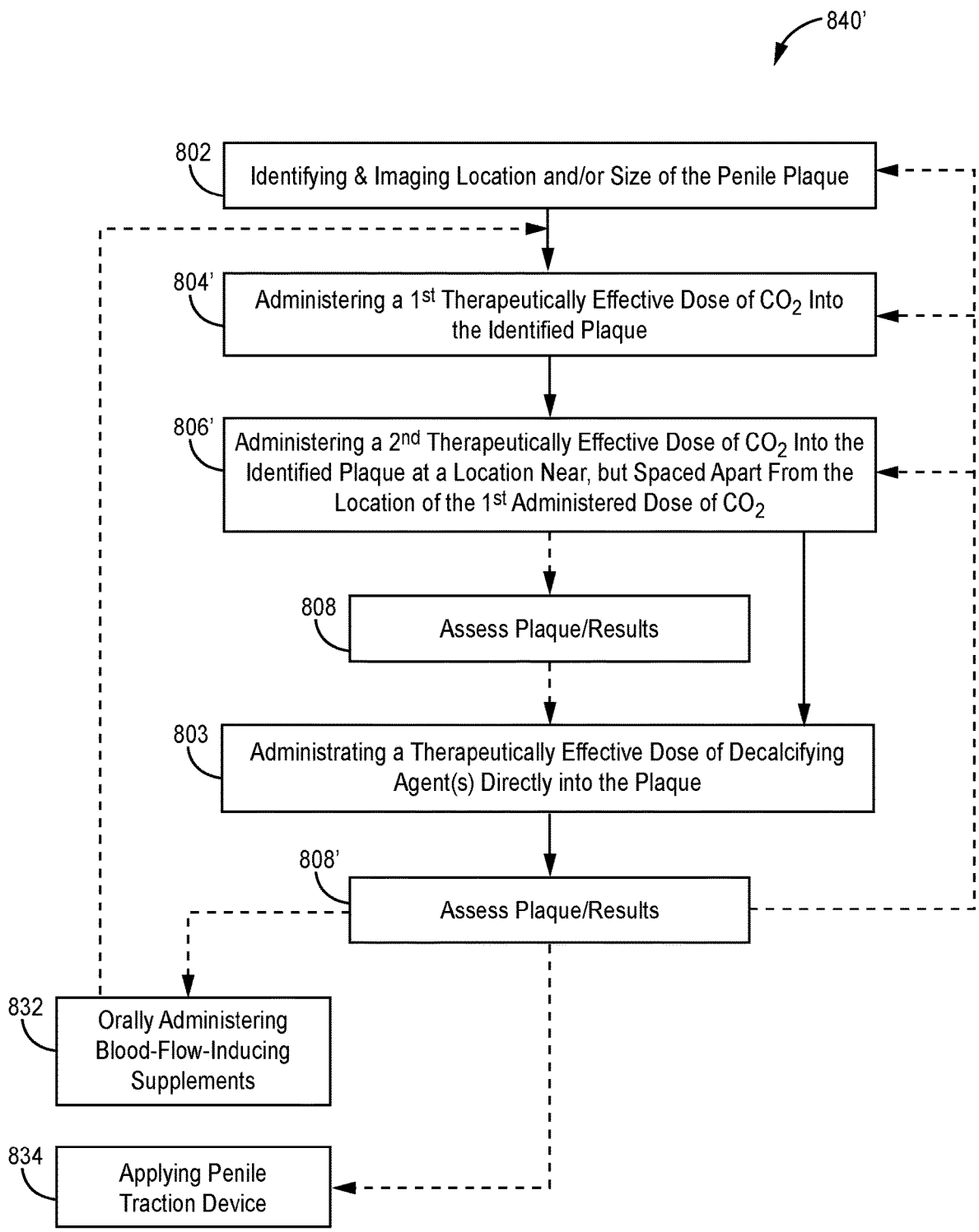
FIG. 9E is one embodiment of a treatment method for Peyronie's disease.

Method 840' of FIG. 9E is identical to method 840 of FIG. 8E except that steps 804' and 806' require the 1st and 2nd carbon dioxide injections to be delivered into the identified plaque, with the second injection 806' administered at a location within the plaque that is spaced apart from the location of the first injection 804'.

In addition to the above treatment method embodiments, Applicants have discovered that injection(s) of carbon dioxide is/are also effective to treat a condition related to Peyronie's disease known as "diffuse plaque" comprising plaque that has not assimilated into any hardened singular construct within the penis, but remains in a "diffuse" state throughout. The preferred treatment method is injection(s) of carbon dioxide directly into the affected corpus tissues to treat the diffuse plaque. This form of carbon dioxide injection treatment may be continued until the diffuse plaque has been sufficiently mitigated or eliminated. Preferably, if more than one carbon dioxide injection is required, then the second injection location is optimally spaced away from the location of the first carbon dioxide injection. As above, the "dose" of each carbon dioxide injection(s) is considered to be "therapeutically effective" which is defined as described above in conjunction with "carboxy therapy".

Figure 10:
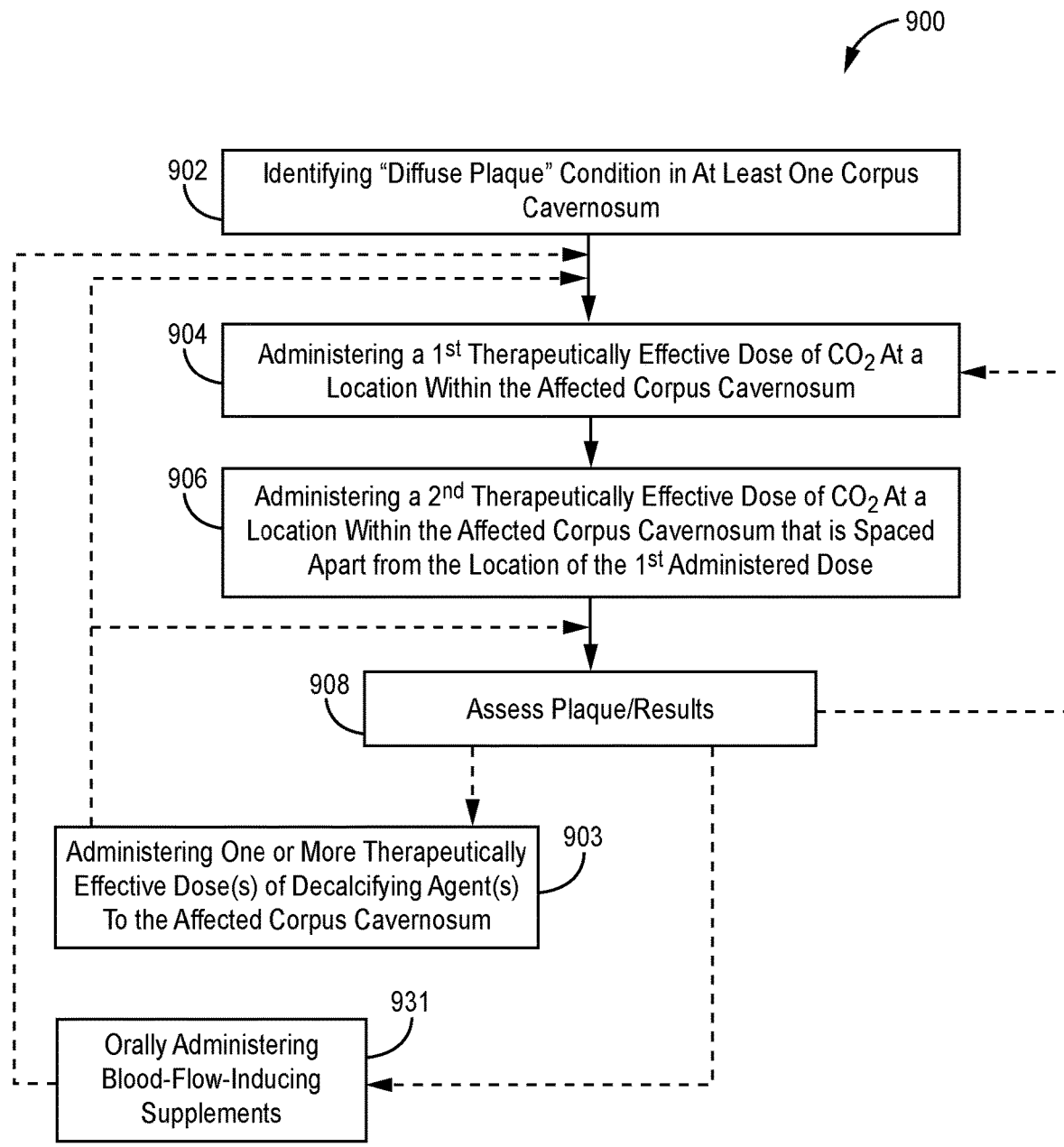
FIG. 10 is one embodiment of a treatment method for "diffuse plaque" within a corpus cavernosum.

FIG. 10 illustrates one method 900 for treating diffuse plaque using the above-described method steps. Thus, the "diffuse plaque" condition is identified or diagnosed within at least one corpus cavernosa at 902. Next, a $1^{st}$ therapeutically effective dose of $CO_2$ is administered by injection to a location within the affected corpus cavernosum at 904. Then, a $2^{nd}$ therapeutically effective dose of $CO_2$ may be administered (this step may be optional) by injection to the affected corpus cavernosum at 906. Note that additional administrations or injections of $CO_2$ as in 904 and/or 906 may also be delivered to unique locations within the affected corpus cavernosum. After the initial round of administration/injection(s) of carbon dioxide is complete, the results may be assessed to see if the plaque is mitigated at 908. If not, the process beginning with step 904 may be repeated. Dashed lines indicate optional steps in the method 900. Thus, step 903 administers a therapeutically effective dose of a decalcifying agent(s) such as discussed herein. As indicated, step 903 may be administered before step 902 or after step 906. Similarly, and as described herein, orally administered blood-flow-inducing vitamin supplements at 932 may be inserted into the method 900 as illustrated by the dashed lines.

Alternative treatment method steps for Peyronie's disease and/or diffuse plaque, in addition to the carbon dioxide injection(s) described above, may further comprise direct injections of recognized decalcification drugs directly into the plaque in the exact area where we will be treating, just before, or just after, employing our new embodiment of carbon dioxide injection(s). Exemplary decalcification agents include Verapamil and Trental. Working examples for this alternative treatment method results in a preference for injecting Verapamil on cases with fibrous plaque and a preference for injecting Trental in patients where plaque has become calcified.

We may also utilize medical penile traction devices and take specific supplements—all of which help with improving penile blood flow, as alternative method steps.

Accordingly, we have developed a novel process utilizing carboxy therapy as shown in the Figures, using a pair of new techniques that may include repeated direct injections into the corpus cavernosum near the plaque and "over and under" the plaque within the corpus cavernosum, that can dramatically impact disease progression, soften the plaque to a point where subsequent collagenase-based injection solutions can achieve far more significant effectiveness or completely dissolve the plaque for reabsorption by white blood cells. We also may utilize direct injections of recognized decalcification drugs directly into the plaque in the exact area where we will be treating, just before employing our new embodiment of carbon dioxide injections. These agents include Verapamil and Trental. Results are best using Verapamil on cases with fibrous plaque and Trental in patients where plaque has become calcified.

In the case of "diffuse plaque"—plaque that's presently not assimilated into a hardened singular construct within the penis, but remains in a diffuse state throughout the corpus—we treat by injecting carbon dioxide as described above directly into the affected corpus tissues until the diffuse plaque is completely eliminated.

Finally, we also congruently employ some recognized supporting Peyronie's treatment therapies that are helpful with optimization of blood flow including:

(1) Stretching of the penis to enhance blood flow during carbon dioxide treatments daily, utilizing either a discreet under-the-pants bungee style penile traction device for as long the patient can endure regularly, e.g., each day for a period of time, and/or a weights-based penile traction system each day and/or regularly for a period of time—ideally 30 minutes in the morning and 30 minutes at night.

(2) Taking blood flow inducing vitamin supplements, including:

l-arginine: A precursor to nitric oxide, a vasodilator. Increases blood flow.

Curcumin: Thought to slow down the progress of arteriosclerosis through limiting the ability of cholesterols to stick to the arterial walls, therefore preventing continued reduction of restrained blood flow associated with a Peyronie's indication.

Omega-3 Fatty Acids: Thought to slow down the progress of arteriosclerosis by reducing the levels of cholesterols in the blood which serves as a building block for penile blood flow inhibition.

Each treatment cycle according to the above may begin with a penile doppler ultrasound to determine the exact size and location of all penile plaque, the present penile blood flow rates, bilateral symmetry and speed (peak systolic velocity) functioning throughout the corpus and coming into the penis from the main arterial veins. These created images represent the outline for our "demolition drawings" when it comes to plaque dissemination—they illustrate exactly where we will be injecting CO2 with our new intracorporeal techniques throughout the penis.

The exact number of intracorporeal CO2 injection treatments required for patient success varied based upon the size and density of penile plaque and existing blood flow rates into the penis and around the plaque and corpus.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A method for treating Peyronie's disease, comprising:
identifying and imaging the location and size of a penile plaque deposit within an affected corprus cavernosum;
administering a first therapeutically effective dose of carbon dioxide by injection to a first location within the affected corpus cavernosum that is adjacent to, and spaced away from, the plaque deposit; and
administering a second therapeutically effective dose of carbon dioxide by injection to a second location within the affected corpus cavernosum that is adjacent to, and spaced away from, the plaque deposit and further spaced away from the first location.

2. The method of claim 1, further comprising administering by injection a therapeutically effective dose of at least one decalcifying agent directly into the plaque deposit before administering the first therapeutically effective dose of carbon dioxide.

3. The method of claim 2, wherein the at least one decalcifying agent comprises Verapamil and/or Trental.

4. The method of claim 2, further comprising orally administering one or blood-flow-inducing supplements selected from the group consisting of: 1-arginine; curcumin; and omega-e fatty acids.

5. The method of claim 1, further comprising administering by injection a therapeutically effective dose of at least one decalcifying agent directly into the plaque deposit after administering the first therapeutically effective dose of carbon dioxide.

6. The method of claim 5, wherein the at least one decalcifying agent comprises Verapamil and/or Trental.

7. The method of claim 5, further comprising further comprising orally administering one or blood-flow-inducing supplements selected from the group consisting of: 1-arginine; curcumin; and omega-e fatty acids.

8. The method of claim 2, further comprising the daily applying of a penile traction device to stimulate blood flow.

9. A method for treating Peyronie's disease, comprising:
identifying and imaging the location and size of a penile plaque deposit within an affected corpus cavernosum;
administering a first therapeutically effective dose of carbon dioxide by injection at a first location within the affected corpus cavernosum that is adjacent to and spaced away from the plaque deposit, and superior to the plaque deposit;
administering a second therapeutically effective dose of carbon dioxide at a second location within the affected corpus cavernosum that is:
adjacent to,
spaced away from the plaque deposit,
inferior to the plaque deposit, and
spaced away from the first location; and
assessing the results of the administered first and second doses of carbon dioxide.

10. The method of claim 9, further comprising administering by injection a therapeutically effective dose of at least one decalcifying agent directly into the plaque deposit before administering the first therapeutically effective dose of carbon dioxide.

11. The method of claim 10, wherein the at least one decalcifying agent comprises Verapamil and/or Trental.

12. The method of claim 10, further comprising orally administering one or blood-flow-inducing supplements selected from the group consisting of: 1-arginine; curcumin; and omega-e fatty acids.

13. The method of claim 9, further comprising administering by injection a therapeutically effective dose of at least one decalcifying agent directly into the plaque deposit after administering the first therapeutically effective dose of carbon dioxide.

14. The method of claim 13, wherein the at least one decalcifying agent comprises Verapamil and/or Trental.

15. The method of claim 13, further comprising further comprising orally administering one or blood-flow-inducing supplements selected from the group consisting of: 1-arginine; curcumin; and omega-e fatty acids.

16. The method of claim 10, further comprising the daily applying of a penile traction device to stimulate blood flow within the patient's penis.

17. A method for treating Peyronie's disease, comprising:
   identifying the location and size of a penile plaque deposit within an affected corpus cavernosum;
   administering a first therapeutically effective dose of carbon dioxide by injection to a first location within the corpus cavernosum that is adjacent to, and spaced away from, the plaque deposit;
   administering a second therapeutically effective dose of carbon dioxide by injection to a second location within the affected corpus cavernosum that is adjacent to, and spaced away from, the plaque deposit and further spaced away from the first location; and
   causing the plaque deposit to soften as a result of the administered first and second therapeutically effective doses of carbon dioxide; and
   subsequently administering by injection a therapeutically effective dose of collagenase clostridium histolyticum into the penile plaque deposit.

18. The method of claim 17, further comprising administering by injection a therapeutically effective dose of at least one decalcifying agent directly into the plaque deposit before administering the first therapeutically effective dose of carbon dioxide.

19. The method of claim 18, wherein the at least one decalcifying agent comprises Verapamil and/or Trental.

20. The method of claim 17, further comprising orally administering one or blood-flow-inducing supplements selected from the group consisting of: 1-arginine; curcumin; and omega-e fatty acids.

* * * * *